United States Patent [19]

Deutsch

[11] Patent Number: 4,921,788

[45] Date of Patent: May 1, 1990

[54] COMPETITIVE NUCLEIC ACID IMMUNOASSAY FOR THE DETECTION OF ANALYTES

[75] Inventor: Dale G. Deutsch, Stony Brook, N.Y.

[73] Assignee: The Research Foundation of State University of New York, Albany, N.Y.

[21] Appl. No.: 180,543

[22] Filed: Apr. 12, 1988

[51] Int. Cl.$^5$ .................... C12Q 1/68; G01N 33/535; G01N 33/545

[52] U.S. Cl. .......................... 435/6; 435/7; 435/810; 436/531; 436/810; 935/77; 935/78; 422/61

[58] Field of Search ............... 435/6, 7, 810; 436/810, 436/531; 935/77, 78; 422/61

[56] References Cited

U.S. PATENT DOCUMENTS

| | | |
|---|---|---|
| 4,205,952 | 6/1980 | Cais . |
| 4,490,472 | 12/1984 | Gottlieb . |
| 4,562,159 | 12/1985 | Shafritz . |
| 4,563,417 | 1/1986 | Albarella et al. ....................... 435/6 |
| 4,600,690 | 7/1986 | Karmen et al. . |
| 4,748,111 | 6/1988 | Duttagupta ........................... 435/7 |

OTHER PUBLICATIONS

Analytical Aspects of Drug Testing, "Ch2-EMIT Assays for Drugs of Abue" by Smith et al., Deutsch, D. G. (Ed.), vol. 100 in Chemical Analysis Series, Wiley, N.Y., N.Y. (1989). Title only.

Zettner, "Principles of Competitive Binding Assays (Saturation Analyses). I. Equilibrium Techniques", Clin. Chem., 19/7, 699-705 (1973).

Zettner, et al., "Principles of Competitive Binding Assays (Saturation Analyses). II. Sequential Saturation", Clin. Chem., 2011, 5-14 (1974).

Kiser, et al., "Solid Phase Extraction of Delta 9-Carboxy-THC From Urine Research & Development Laboratories," J. T. Baker Chemical Company, Phillipsburg, N.J. 32, 1115 (1986).

Wisdom, Clinical Chemistry, vol. 22, pp. 1243-1255, 1976.

Cook, et al., NIDA Research Monograph Senis, vol. 7, pp. 15-27, 1976.

Zuk, et al., Clinical Chemistry vol. 31, pp. 1144-1150, 1985.

Nabarro, Radioimmunoassay and Saturation Analysis, Brit. Med. Bull, 30, 1-3 (1974).

Voller, et al., The Enzyme Linked Immunosorbent Assay (ELISA) Dynatech Labs, Inc. Alexandria, Va., 1-125 (1979).

Rubenstein, et al., "Homogeneous" Enzyme Immunoassay. A New Immunochemical Technique, BBRC, 47, 846-851 (1972).

Emancipator, K. and Deutsch, D. G., Dry Reagent Chemistries in Toxicology, (Ed. Deutsch, D. G.), in Analytical Aspects of Clinical Toxicology, Chemical Analysis Series, Wiley, New York (In Press 1988).

Litman, et al., An Internally Referenced Test Strip Immunoassay for Morphine, Clin. Chem. 29, 1958-1603 (1983).

(List continued on next page.)

*Primary Examiner*—Christine M. Nucker
*Assistant Examiner*—Karen Krupen
*Attorney, Agent, or Firm*—Hoffmann & Baron

[57] ABSTRACT

A kit and a method for performing a competitive immunoassay utilize nucleic acid oligonucleotide chains for the detection of analytes, such as drugs, substances of abuse, hormones, poisons, organic compounds, peptides, proteins and the like. The kit includes a hapten-oligonucleotide complex, a complementary oligonculeotide chain for conjugating with the hapten-oligonucleotide complex, an antibody specific for the hapten and a flourescent label such as ethidium bromide having an affinity for nucleic acid duplexes formed from the hapten-oligonucleotide complex and the complementary oligonucleotide chain. A means for detecting the presence of the florescent label such as a U.V. transilluminator, U.V. lightbox and fluorescence spectrophotometer is utilized to detect color intensity and fluorescence of the dye. The method can be performed in solution, or on a solid "dipstick" on which the reagents for the immunoassay have been immobilized.

26 Claims, 2 Drawing Sheets

ANALYTE PRESENT　　Fig.1A
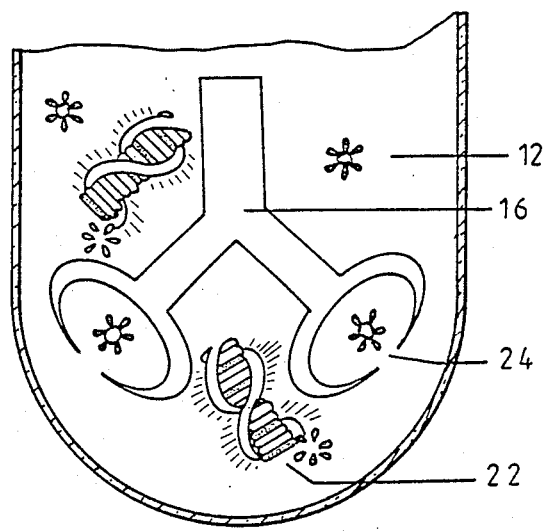
ANALYTE ABSENT　　Fig.1B
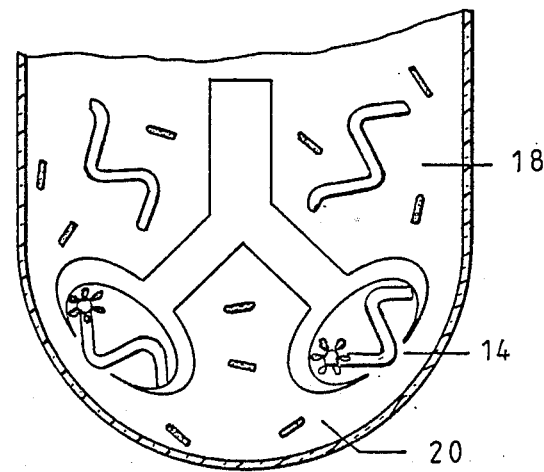

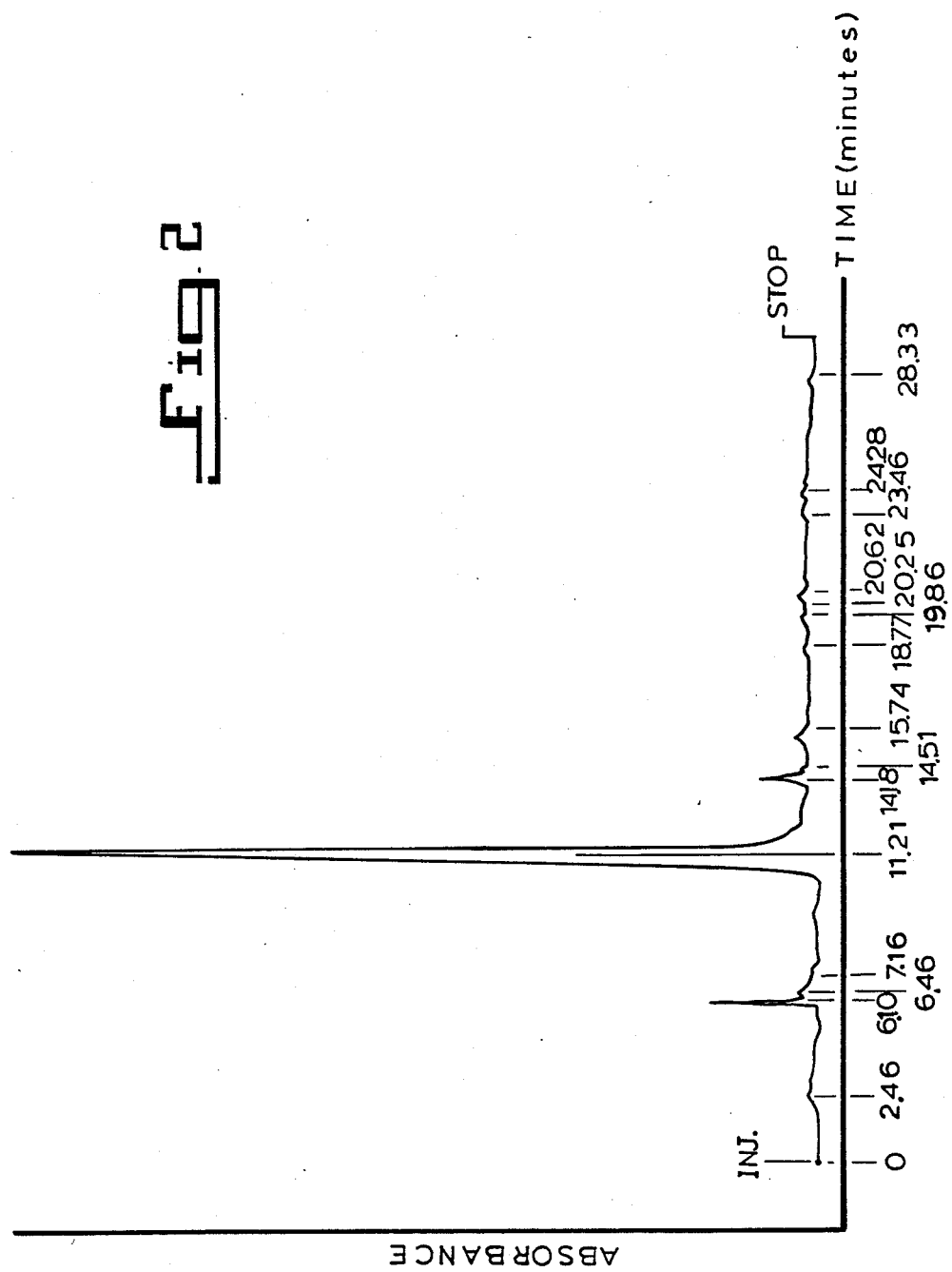

COMPETITIVE NUCLEIC ACID IMMUNOASSAY FOR THE DETECTION OF ANALYTES

BACKGROUND OF THE INVENTION

The United States Government has certain rights in this invention pursuant to NIH Biomedical Research Support Grant No. 431-E282N.

FIELD OF THE INVENTION

This invention relates to competitive immunoassays for the detection of analytes, such as drugs, hormones, organic compounds, peptides and proteins, which uses nucleic acid chains and fluorescent dyes as reagents.

BACKGROUND OF THE RELATED ART

Misuse of controlled substances, including drugs of abuse and steroids, have recently become the focus of media attention and regulatory activity in both the private and public sectors. Many agreements between athletes and the management of professional sports teams provide for random testing for drugs of abuse such as opiates, cocaine and cannabis.

Likewise, there are now provisions which require drug testing for many federal and state employees in key positions. Moreover, emergency situations due to drug overdose and poisoning require immediate diagnosis and treatment. Often, in such emergency situations the results of blood, urine and saliva tests which must be sent to laboratories, arrive too late to save the victim. Many of these tests are difficult to administer and require trained personnel who are often unavailable in emergency situations. Accordingly, there has long been a need for an assay which is simple to administer and which provides an immediate and accurate determination of the presence of a specific drug or poison in the body fluids of the test subject, whether the subject is an incoherent or unconscious victim, or a suspected drug abuser.

A variety of immunoassays have previously been developed, these include: radioimmunoassays ("RIA"), homogeneous enzyme-multiplied immunoassays ("EMIT"), enzyme linked immunoadsorbent assays ("ELISA"), apoenzyme reactivation immunoassay ("ARIS"), dipstick immunoassays and immunochromotography assays.

The most widely used of these are the RIA; see, Nabarro, *Radioimmunoassay and Saturation Analysis*, Brit. Med. Bull, 30, 1-103 (1974); the ELISA, see, Voller, et al., *The Enzyme Linked Immunosorbent Assay (ELISA)*. Dynatech Laboratories, Inc., Alexandria, Va. 1-125 (1979); and the EMIT, see, Rubenstein, et al., *"Homogeneous" Enzyme Immunoassay. A New Immunochemical Technique*, BBRC, 47, 846-851 (1972).

RIA techniques are very sensitive, however, the radioactive isotopes used in these techniques require complex equipment for reading the results of the RIA and special safety measures for the use and disposal of the radioactive isotopes. Heterogeneous enzyme immunoassays such as the ELISA, require the separation of enzyme-labeled substance from unreacted enzyme-labeled material. These assays are most commonly used for the analysis of large molecules.

An improvement to the heterogeneous binding immunoassays is described by Cais, in U.S. Pat. No. 4,205,952 for the detection of various metabaloids, drugs and the like. The technique utilizes a binding component, and a labelled metallic constituent that can be detected. The labelled metallic constituent includes one or more metal atoms which can be detected, and are present in the form of a variety of metalo organic derivaties or metal coordination complexes. Although this technique does not use radioactive isotopes, it is time consuming, complex and still requires a variety of equipment for the separation of the bound-phase from the free-phase by filtration or centrifugation, and the detection of metals by emission, absorption, and fluorescence spectronomy.

In the detection of small molecules, however, the EMIT system is most prevalent. In the EMIT system, a hapten is linked to an enzyme and the activity of the enzyme is inhibited when an antibody is combined with the hapten-enzyme conjugate. The assay system contains an enzyme-hapten also called an "enzyme-analyte", an antibody, an enzyme substrate and a test sample. If the test sample contains any of the analyte, it will combine with the antibody leaving the enzyme-analyte conjugate free to react with the substrate. Conversely, if there is no analyte present in the test sample, the activity of the enzyme will be inhibited by its interaction with the antibody.

Refinements in the EMIT techniques have resulted in more rapid and accurate immunoassays. For example, Karmen et al., U.S. Pat. No. 4,600,690 disclose an EMIT type immunoassay. In this immunoassay an excess amount of unlabeled antigen is added after the start of the reaction between the labeled hapten (ligand), the unlabeled ligand (hapten) and the antibody, in order to saturate the binding sides of the antibody. This technique provides increased sensitivity in the competitive binding immunoassay. However, it requires precise measurements in the laboratory and highly trained personnel to conduct the assay. In addition, it does not provide for instantaneous test results.

Recently, attention has focused on placing the components of these immunoassays on a solid phase. The goal is to produce a one step dipstick immunoassay. A comprehensive discussion of the use of reagent strips for various immunoassays has been co-authored by the inventor, herein, and is will soon be published. See, Emancipator, K., and Deutsch, D. G., *Dry Reagent Chemistries in Toxicology*, (Ed. Deutsch, D. G.), in Analytical Aspects of Clinical Toxicology, Chemical Analysis Series, Wiley, N.Y. (In Press 1988). For example, as discussed therein, Litman, et al. disclose a qualitative dipstick for testing of morphine in urine; see, Litman, et al., *An Internally Referenced Test Strip Immunoassay for Morphine*, Clin. Chem. 29, 1958-1603 (1983). This immunoassay uses the enzymechanneling of glucose oxidase-horseradish peroxidase to immunospecifically generate an insoluble reaction product on the surface of a test strip. The test strip also contains an antibody specific for morphine which inhibits the development of color on the test strip when the antibody combines with morphine in the test sample.

There have also been publications describing dry-reagent strips for testing levels of theophylline, a potent bronchodilator used to treat acute and chronic asthmatic symptoms. Concentrations of theophylline over 10 to 20 mg/l are associated with toxic symptoms, such as nausea, vomiting, headaches, and in extreme cases convulsions and death. A method developed by Rupchock et al., in *Dry-Reagent Strips Used for the Determination of Theophylline in Serum*, Clin. Chem. 31, 731-740 (1985), which is based in Serum, Clin. Chem.

31, 731–740 (198 upon the ARIS system. Rupchock et al. disclose that theophylline competes with theophylline conjugate labeled with flavine adenine dinucleotide for a limited number of antibody binding sites. The antibody is incorporated into a reagent strip. In the absence of theophylline in the blood serum of the patient, the conjugate binds to the antibody and is not available for further reaction with apoglucose oxidase. Apoglucose oxidase is detected by the presence of a colored product, produced by a coupled reaction of Apoglucose oxidase with peroxidase and other reagents impregnated on the filter paper test strip. The intensity of color is proportional to the concentration of the theophylline in the specimen and can be quantitatively analyzed using a reflectance photometer. One drawback of this method is that it requires the separation of blood serum from whole blood, prior to testing.

Another method which utilizes a solid phase for the detection and analysis of theophylline uses an immunochromatographic assay developed by Zuk et al., in *Enzyme Immunochromatography-A Quantitative Immunoassay Requiring No Instrumentation*, Clin. Chem., 31, 1144 (1985). This method does not require separation steps and can be performed on whole blood without using any detection instruments. In this method, the sample drug ("antigen") and an antigen-enzyme conjugate are first combined, and a paper strip on which an antibody has been immobilized is dipped into this combined sample, allowing the sample to move up paper strip by capillary action. After color development due to peroxidase reaction, the result of the assay is obtained by reading the height of the colored zone on the test strip. The reaction takes approximately fifteen minutes.

All of the immunoassays which take advantage of the affinity of the hapten-enzyme complex for the antibody in competition with the affinity of the antigen/analyte for the antibody, are subject to specific binding strengths of the enzyme/substrate combination, which can not be varied. It would be desirable, however, for an investigator to have the flexibility to vary the binding strengths of the reagents in an immunoassay, instead of being locked into the classical enzyme-substrate interactions. In addition, the use of enzymes in an immunoassay result in several other disadvantages, including lack of stability due to denaturation of the enzymes, temperature dependance, pH dependance and ionic strength (salt) dependance. For example, many EMIT tests can be fooled into registering a false negative by high salt concentrations or pH variations in the test sample.

Prior to the present invention, nucleic acids have not been used as reagents for immunoassays. Nucleic acids have been used, however, for diagnostic tests, as probes detecting the DNA of infective agents such as that of a virus, or malignant tissue. Thus, Schafritz U.S. Pat. No. 4,562,159 discloses a hybridization probe prepared from hepatitis B-virus DNA (HBV-DNA) labeled with highly radioactive substances such as $^{32}P$ or $^{125}I$. The hybridization probe is combined with a test sample suspected of containing hepatitis B-virus. Following incubation, the combined HBV-DNA probe is removed from the substrate and the presence of hybridized HBV-DNA is determined by liquid scintillation spectroscopy or by autoradiography of the substrate. In addition, Gottlieb U.S. Pat. No. 4,490,472 discloses a test for malignancies based on DNA detection. According to this test, sera from a test subject is mixed with labeled DNA in the presence of an enzyme-conjugated resin. Sera from normal and malignant tissue have different degrees of affinity and react differently with the resin, permitting a diagnosis of a malignancy.

Accordingly, an object of the present invention is to provide an immunoassay for testing body fluids for poisons, toxins and drugs of abuse which would permit quick screening in emergency situations.

Another object of the present invention is to provide an assay which allows personnel which are not familiar with complex laboratory techniques to use the assays in emergency situations.

A further object of the present invention is to provide an assay which allows for the custom preparation of reagents with specific binding strengths to provide an extremely reliable and sensitive immunoassay.

Still, a further object of the present invention is to provide an immunoassay with reagents which are extremely stable and relatively insensitive to variations in temperature, pH and ionic concentrations of the sample.

SUMMARY OF THE INVENTION

The present invention provides a competitive immunoassay which advantageously utilizes the properties of complementary oligonucleotides for the detection of analytes such as drugs, substances of abuse, hormones, poisons, organic compounds, peptides, protein and the like. In accordance with the present invention, a sample analyte and an analyte-oligonucleotide conjugate react in the presence of an antibody specific for the aralyte or to a closely related structure ("hapten"). A complementary oligonucleotide chain conjugating with the haptenoligonucleotide complex is also provided. A fluorescent label such as ethidium bromide, which has an affinity for the nucleic-acid duplex is included to label the nucleic acid duplex in the event that no analyte is present in the sample.

Accordingly, if the sample does not contain the analyte, the antibody will bind to all analyteoligonucleotide conjugates and prevent intercalation of the fluorescent dye within the nucleic acid duplex, preventing color development. If the sample contains sufficient analyte, the analyte will fill the available antibody binding sites and leave the hapten-oligonucleotide complex free to bind with the complementary oligonucleotide chains resulting in intercalation of the fluorescent dye within the duplex and color development. Color development, intensity and fluorescence of the dye may be detected using a short wave U.V. transilluminator, a U.V. lightbox, or a fluorescence spectrofluorimeter. The immunoassay may be conducted in a liquid solution, or the immunoassay reagents may be immobilized upon a solid "dipstick" which can be inserted into a liquid sample in order to perform a one step immunoassay.

Accordingly, the present invention takes advantage of recent advances in oligonucleotide sequencing and synthesis technology to allow the investigator the freedom to specifically synthesize whatever combination of complementary oligonucleotide chains are desired. Thus, complementary oligonucleotide chains with various binding strengths, may be supplied in a kit to customize the immunoassay and to provide a much more specific and predictable immunoassay than could be achieved with the traditional enzyme dependant systems.

The present invention takes advantage of the affinity of complementary oligonucleotide chains for use as immunoassay reagents, instead of enzymes and the interaction with their substrates, to provide an immunoassay which solves the problems inherent in enzymedependant immunoassays.

By contrast to the unstable enzymes, oligonucleotide chains are not subject to denaturation and, thus, are extremely stable. The interaction of oligonucleotide chains is relatively unaffected by variations in temperature, pH and ionic strength of the sample.

BRIEF DESCRIPTION OF THE DRAWINGS

FIG. 1A schematically illustrates the interactions in a nucleic acid immunoassay, according to the present invention when the analyte or drug which is being tested is present in the test sample.

FIG. 1B schematically illustrates the interactions in a nucleic acid immunoassay, according to the present invention, when the analyte or drug which is being tested is absent from the test sample.

FIG. 2 is a high performance liquid chromatogram (HPLC) illustrating the purification of the THColigonucleotide complex described in Example 1C.

DETAILED DESCRIPTION OF THE PREFERRED EMBODIMENTS

The present invention provides a competitive immunoassay for the detection of analytes, such as drugs, substance of abuse, hormones, poisons, organic compounds, peptides, proteins and the like, using nucleic acid oligonucleotide chains and a fluorescent dye as reagents. As illustrated in FIGS. 1A and 1B, sample analyte 12 and analyteoligonucleotide conjugate 14 are allowed to react in the presence of antibody 16 specific for the analyte 12, or to a structure closely related to the analyte, called the hapten. A complimentary oligonucleotide chain 18 and a fluorescent dye 20, such as ethidium bromide, are also provided. If the sample does not contain sufficient analyte, as illustrated in FIG. 1B, the antibody 16 will bind all analyteoligonucleotide conjugates 14 and prevent the formation of nucleic acid duplexes 22, thus preventing color development. However, as illustrated in FIG. 1A, if the sample contains the sufficient analyte 12, the analyte 12 will fill the available antibody binding sites 24 and leave the labeled oligomers 14 free to form duplexes 22 with complimentary oligonucleotide chains 18. Oligonucleotide duplex formation 22, as illustrated in FIG. 1A results in dye intercalation and color development (see 22). Color development increases in proportion to the concentration of analyte present in the sample.

Any combination of complimentary oligonucleotide chains can be synthesized so that the investigator can specifiy the composition of the chain, its length, and the binding strength between complimentary oligonucleotide chains. Such specifity cannot be achieved by prior enzyme dependent immunoassays since each enzyme-substrate combination has a specific binding strength which could not be varied.

The detection of the active components of marijuana provides one preferred application of the present invention. Marijuana is a complex mixture of over 400 individual chemicals of which 9-tetrahydrocannabinol (9-THC) is the major psychoactive component. After smoking marijuana, the major urine metabolite is the 11-nor-9-tetrahydrocannabinol-9-carboxylic acid (9-THC-COOH) which exists in urine, partially, as a glucuronide conjugate; see, Hawks, *The Constituents of Cannabis and the Disposition and Metabolism of Cannabinoids,* Research Monograph, 42, National Institute of Drug Abuse, 125–137 (1982).

The analysis of urine provides an indication of the use of cannabis while analysis of the level of 9-THC in blood provides the best indicator of intoxication.

A series of cannabinoid analogs (haptens) have been synthesized and complexed to albumin. From this work, antibodies with different selectivies to cannabinoid haptens have become available; see, Cook, et al., *Radioimmunoassay of α 9-Tetrahydrocannabinol,* NIDA Research Monograph Series, 7, 15–27 (1976). Similarly, in this invention cannabinoid analogs have been selected which are suitable for coupling to oligonucleotides in a similar manner as previously coupled to the protein albumin.

CONJUGATION OF CANNABINOIDS TO OLIGONUCLEOTIDES

Complementary oligonucleotides have been synthesized at the Center for Analysis and Synthesis of Macromolecules in the University Hospital at the State University of New York at Stony Brook. Optionally, they may be purchased from such companies as Synthetic Genetics in San Diego, Calif. Oligonucleotides have been synthesized by phosphite-triester solid-phase method and purified from contaminating oligomers by HPLC; see, Regnier, *HPLC of Proteins, Peptides and Polyonucleotides,* Anal. Chem. 55, 1298a (1983). Recent methods which have been developed, to allow the introduction of an aliphatic primary amino group at the 5' terminus of a synthetic oligonucleotide, may be used in the present invention, as described by Coull et al., in *A Novel Method for the Introduction of an Aliphatic Primary Amino Group at the 5' Terminus of Synthetic Oligonucleotides,* Tetrahedon Lett, 27, 3991–3994 (1986). Such reagents are now commercially available, for example from Applied Biosystems, Santa Clara, Calif., under the trademark Amino-Link for use with DNA synthesizers. In addition, amino groups may be introduced within the oligonucleotide for subsequent coupling according to the method of Jablonski, et al., described in *Preparation of Oligodeoxynucleotide-Alkaline Phosphatase Conjugates and Their Use as Hybridization Probes,* Nucl. Acid. Res., 14, 6115–6128 (1968).

Various methods have been developed to allow the coupling of cannabinoids to primary amino groups on proteins, i.e. for antibody reproduction; see, Tsui et al., $\Delta^9$-*Tetrahydrocannabinol-Protein Conjugates.* Can. J. Biochem., 52, 252–258 (1974). Such coupling methods are easily adapted for coupling of cannabinoids to $H_2N$-oligonucleotides. One preferred approach is to succinylate the phenolic hydroxyal group of THC and then couple the resulting hemisuccinate to the $H_2N$-oligonucleotide using dicyclohexyl-carbodiimide. Another preferred method is to use THC which has been modified to contain a carboxyl group on the 5' position on the aliphytic chain, as disclosed by Cook, et al., in *Radioimmunoassays for Cannabinoids,* NIDA Research Monograph Series, 42, 19–31 (1982). The 5'-carboxyl-9-THC analog may be purchased from Research Triangle Institute, Research Triangle Park, N.C. and treated with N-hydroxysucciniminde and diclyohexyl-carbodiimide to yield an ester. The ester reacts readily in mixture of dioxane and sodium bicarbonate with the aliphatic primary amino group at the 5' terminus of the synthetic oligonucleotide.

However, for the purpose of illustrating the nucleic acid immunoassay, the utilization of 9-THC-hemisuccinic acid for coupling is the preferred method since antibodies to 9-THC and 9-THC-COOH both react with the THC-hemisuccinate hapten. Antibodies required for the present invention are obtained from a variety of sources including Genetic Diagnostic Corporation, Great Neck, N.Y. and Research Triangle Institute, Research Triangle Park, N.C.

ASSAY FORMAT

The nucleic acid immunoassay of this invention is designed for use in a variety of formats. The simplest approach, which was used for initial research and developments purposes, is to perform the assay in a solution phase. The assay is performed semi-quantitatively using a U.V. transilluminator with all the components applied as a drop on a glass plate. The assay is also conducted in the solution phase, in a quartz or glass cell, using a spectrofluorimeter which permits a more quantitative measure and greater selectivity over the excitation and emission wavelengths of the specific source of light used. The wavelength for an excitation and emission depends on a specific dye that is employed. For example, when ethidium bromide was used, the excitation wavelength of 306 $\eta$m or 524 $\eta$m was found to yield a maximum photon emission at 612 $\eta$m.

Another format for the nucleic acid immunoassays is through the use of dry test strips ("dipsticks"). The dipstick contains the antibody and THC-oligonucleotide applied in such a manner that they do not react until the dipstick is wetted. The dipstick can then be wetted with the sample being tested. Thereafter, the dipstick is immersed in a developer solution which contains complementary synthetic oligonucleotide chains and a fluorescent dye such as ethidium bromide as a label. After development, the final color intensity is read quantitatively in a U.V. light box or quantitatively with a reflectance photometer using long wavelengths U.V. for excitation. Preferably, the label (dye) is covalently bound to either the hapten-oligonucleotide complex or the complementary oligonucleotide chain. Thus, if the sample contains nucleic acids, for example in tissue samples, the free label cannot attach to nucleic acids from the sample and ruin the assay. By covalently binding the label to either oligonucleotide chain the label will only attach itself to duplex nucleic acid chains supplied by the immunoassay, rather than from the sample.

The immunoassay of the present invention can, for example, use an antibody which binds very strongly to the analyte-oligonucleotide conjugate, while the interaction between complementary oligonucleotide chains can be made to be very weak. Thus, if all antibodies sites are not filled by analyte, the antibody could separate a pre-existing oligonucleotide duplex, to allow for a one step immunoassay.

Especially preferred, is a dipstick which contains the antibody, the THC oligonucleotide, the complementary oligonucleotide and the label, such as ethidium bromide, all in a dry, unreacted state. Thus, a drop of sample such as urine can be added to the dipstick or the dipstick dipped in the sample, to perform a one step immunoassay. If the sample does not contain THC, the antibody will combine with the THC-oligonucleotide conjugate and prevent nucleic acid duplex formation and color development. Alternatively, if the sample does contain THC, the THC will fill the antibody binding sites and leave the THC oligomer free to form duplex structures with complementary chains resulting in dye intercalation and color development.

CONCENTRATION AND LENGTH OF OLIGONUCLEOTIDE CHAINS

The effect of the concentration and structure of oligonucleotides upon specific assay perameters are important for the development of each specific assay. The starting point for developing a specific assay is to establish baseline concentrations of assay components for conveniently monitoring the assay, using two complementary oligonucleotide chains and a dye. For example, to establish a baseline, oligo-$(dA)_x$ and oligo-$(dT)_x$ and a dye are mixed on a U.V. transilluminator with varying concentrations of intercalating dye, and the response is recorded.

Once the baseline for oligonucleotide dye concentrations is established, the effect of binding the analyte and/or dye to the oligonucleotide chain on duplex formation (hybridization) is determined. Thus, oligo-$(dT)_x$, oligo-$(dA)_x$, and a dye are mixed on a U.V. transilluminator with a varying concentration of intercalating dye. The results are recorded and compared to those found with unconjugated chains. Fluorescence spectrophotometry is then conducted to obtain quantitative data. Previous studies using DNA on an ethidium bromide have shown that the concentration should be in a low $\mu$g range for visualization of the oligonucleotides. The oligonucleotide concentration is determined by comparison to standards on a light box or spectraphotometrically by absorbance readings at 260 $\eta$m. For example, a 20 $\mu$g/ml sample yields an $OD_{260}$ of 1; see, Maniatis, et al., *Molecular Cloning, A Laboratory Manual*, 468, Cold Spring Harbor Laboratory, N.Y. (1982).

FLUORESCENT PROBES FOR THE VISUALIZATION OF OLIGONUCLEOTIDES

A variety of fluorescent label molecules are available for visually detecting the hybridized oligonucleotide chains. See, Yanagida, et al., *Video-Connected Fluorescence Microscopy of Large DNA Molecules, Chromatin, and Chromosomes* in (Ed. Taylor, D. L. et al.) *Applications of Fluorescence in the Biomedical Sciences*, Alan Liss, New York, chap. 15 (1985). Particularly preferred are DAPI(4', 6-diamidino-2-phenylindole dihydrochloride); DIPI [4', 6-bis(2'-imidazolinyl-4', 5'-H-)2-phenylindoledihydrochloride]; H33258 (Hoechst 33258); acridine orange; acridine yellow; 288/45 [2', 6-bis(2'imidazolinyl-4', 5'-H-)-2', 6-bisindole]; 186/134 {2-[4'(p-amidinophenoxy)phenyl]-6-amidinoindole}; and ethidium bromide. Also see, *Applications of Fluorescence in the Biomedical Sciences*, Proceedings of a meeting held in Pittsburgh, Pa., Apr. 12-15, (Ed. by Taylor et al.), 323, Alan R. Liss, Inc., New York (1975).

The wide selection of dyes makes it possible to use a combination of excitation and emission wavelengths to maximize the desired signal to noise ratio. This is particularly important when biological fluids are used which may, at certain wavelengths, either themselves fluoresce or cause quenching of the intercalated dye. The fluorescence of these dyes is caused by the intercalation of the dye, i.e. presence of the dye within the duplex nucleic acid chain. The fluorescence phenomena of intercalated dyes is discussed by Douthart, et al., in *Binding of Ethidium Bromide to Double-Stranded Ribonucleic Acid*, Biochemistry, 12, 214–219 (1973).

ANTIBODY ANALYTE AND OLIGONUCLEOTIDES

The nucleic acid immunoassay is critically dependant upon the interaction of the chosen antibody with the analyte-oligomer so that the antibody can block the complementary chain from hybridizing and forming a duplex of complementary oligonucleotides. This interaction is similar to the interaction between the antibodies and enzyme in the enzyme-multiplied immunoassays in which enzymatic activity towards low molecular weight substrates is inhibited by the antibody. The results, discussed below, indicate that an antibody towards THC indeed prevents hybridization of the oligonucleotide chains. Thus, the antibody concentration for the nucleic acid immunoassay is adjusted, by dilution, to yield the minimal antibody concentration necessary to inhibit hybridization of the oligonucleotides, for example, of THC-$(dT)_x$ and $(dA)_x$ hybridization.

An important advantage in using oligonucleotides as reagents for the immunoassays, is that &:heir affinity for each other can be custom adjusted by adjusting their length and/or composition. Such manipulation is very convenient, if for example, in the absence of analyte, any antibody and analyte combination yields a significant amount of hybridization between the two chains. This problem can be circumvented by using complementary oligonucleotide chains with a weaker affinity for each other. Also, the analytes can be linked to either end, or to the middle of the oligonucleotide chain to vary the strength of the interaction between the antibody and the analyte-oligomer. Control of these parameters determines the facility with which the analyte competes with the analyte-oligomer and hence the shape of the concentration versus response curve of the immunoassay. The standards for the immunoassay are made, for example, by spiking drug-free urine with 9-THC-COOH, or such standards may be purchased from commercial manufacturers. The assay can be run quantitatively or qualitatively by comparing the color intensity of the sample analyte to negative and positive cannabinoid controls. Selective ion monitoring gas chromatography mass-spectrometry is also used as a quantitative reference method utilizing duterated 9-THC-COOH as the internal standard. Ions of M/Z 371, 473 and 488 atomic mass units are monitored for non-THC-COOH and 491 atomic mass units by detecting the duterated internal standard as disclosed by Kiser, et al., in *Solid Phase Extraction of $\Delta^9$-Carboxy-THC from Urine*, Clin. Chem. 32, 1115 (1986).

The nucleic acid immunoassay of this invention can be adapted to detect other drugs, poisons, etc. as was done with 9-THC. For example, Rubenstein et al. U.S. Pat. No. 3,867,366, which is incorporated herein by reference, discloses the preparation of opiate imidates with proteins conjugated thereto which are useful for the formation of antibodies. Thus the opiate imidiates can be complexed with oligonucleotide chains for use as reagents in a nucleic acid immunoassay for opiates in much the same manner as described above for 9-THC.

DIPSTICK ASSAY-ANTIBODY INSOLUBILIZATION

As described above, the nucleic acid immunoassay is adaptable for use on a solid phase using filter paper or any of the many solid phases that are commercially available, such as Pall Bio Support manufactured by Glen Cove, N.Y. A preferred approach is to immobilize the antibody to the support. For example, aminophenyl-thioether cellulose (paper) may be diazotized with a hydrochloric acid solution of sodium nitrate as described by Renart, et al., in *Transfer of Proteins from gels to diazobenzyloximethyl-paper and detection with antisera: A method for studying antibody specificity and antigen structure*, Proc. Natl. Acad. Scin., 76, No. 7, 3116–3120 (1979). The activated paper is coupled to cannabinoid so that the protein density varies from 5 to 20 $\mu g/cm^2$. Antibody may be either monoclonal or polyclonal and may be obtained from the Research Triangle Institute, Research Triangle Park, N.C. or from Genetics Diagnostics in Great Neck, N.Y. As previously discussed, the THC-hemisuccinate, used for conjugation to the oligonucleotide, reacts with antibodies to both 9-THC and 9-THC-COOH.

EXAMPLE 1

A. Synthesis of Oligonucleotides

Approximately 0.5 mg each of two synthetic polydeoxyribonucleotides, $poly(dA)_{10}$ and $poly(dT)_{10}$, and 100 $\mu g$ $poly(dT)_{10}-NH_2$ have been synthesized in the oligonucleotide synthesis facilities at the University Hospital of the State University of New York at Stony Brook and purified by a high performance liquid chromatography (HPLC).

B. Effects of Ionic Strength and Ethidium Bromide Concentration Upon Hybridization of Oligonucleotides A fluorescence spot test, using a shortwave UV transilluminator manufactured by UVP, San Gabriel, Calif., was performed essentially as described by Kowalski, in *Fluorescence Spot Tests for DNA Endonuclease, Ligase, and Topisomerase Activities*, Anal. Biochem., 107, 311 (1980). Spots were photographed through a red filter. The effect of ionic strength on ethidium bromide ("EthBr") fluorescence was studied. Fixed concentrations of oligonucleotides, both as single chains and duplex, were mixed with ethidium bromide in $H_2O$, and in water containing 0.1 M NaCl buffered to a pH of 7.4 and observed on the U.V. transilluminator. The results of this experiment are shown in Table 1.

TABLE 1

| OLIGONUCLEOTIDE | EthBr(75NG) | |
|---|---|---|
| | $H_2O$ | SALINE |
| NONE | 0 | 0 |
| $(dA)_{10}$ | +++ | 0 |
| $(dT)_{10}$ | +++ | 0 |
| $(dA)_{10} + (dT)_{10}$ | +++ | +++ |

These results show that in water, some fluorescence occurs with single chains, particularly $(dT)_{10}$ and that this fluorescence of single chains is diminished in the presence of the 0.1 M NaCl buffered solution. These results are confirmed by results of studies with DNA and RNA reported by others, such as LePecq, in *Ethidium Bromide: A Fluorescent Probe of Nucleic Acid Structure and Its Potential for In-Vivo Studies*, Anal. Biochem., 17, 100 (1966); and Douthart et al., *Binding of Ethidium Bromide to Double Stranded Ribonucleic Acid*, Biochemistry, 12, 214 (1973). These results show that at low ionic strength (NaCl concentration) secondary bonding occurs between ethidium bromide and the phosphate groups of nucleic acids. However, at high ionic strength these interactions are minimized, so that "sandwiching" of ethidium bromide between the base pairs becomes the only observable source of fluorescence. Accordingly, all experiments with oligonucleotide chains and ethidium bromide are conducted using at least 0.1 M NaCl.

Using a hand-held transilluminator, experiments were conducted to optimize the levels of ethidium bromide concentrations in order to maximize the signal to noise ratio. Table 2 shows a series of experiments where the amount of EthBr was varied over a 100-fold range using a fixed amount of oligonucleotide.

TABLE 2

| OLIGONUCLEO-TIDE | EthBr(NG) | | | | | |
|---|---|---|---|---|---|---|
|  | 5 | 50 | 75 | 125 | 250 | 500 |
| NONE | 0 | 0 | 0 | + | + | ++ |
| $(dA)_{10}$ | 0 | 0 | 0 | + | ++ | ++ |
| $(dT)_{10}$ | 0 | 0 | 0 | ++ | ++ | +++ |
| $(dA)_{10} + (dT)_{10}$ | 0 | 0 | +++ | +++ | +++ | ++++ |

These experiments demonstrate that an optimal concentration of EthBr relative to the oligonucleotide concentration has been determined to be approximately a 2:1 on a molar ratio. In addition, these experiments show that above certain levels, free ethidium bromide provides high background fluorescence which masks the fluorescence of the EthBr intercalated into the oligonucleotide duplex chains. This phenomena has been observed by other researchers at the State University of New York while using fluorescence methods for DNA topoisomerase and endonuclease assays; see Foglesong et al., *Ethidium Bromide Fluorescence Methods for DNA Topoisomerase and Endonuclease Assays*, Unpublished Draft, Department of Microbiology, School of Medicine, State University of New York, Stony Brook, N.Y. (1987).

A preferred embodiment of this invention provides a method for obviating the interference due to the EthBr background. The excitation spectra of EthBr both in the absence of, and in the presence of $(dA)_1 + (dT)_{10}$ was measured by observing the fluorescence at 612 m$\mu$ using a Perkin-Elmer MPF-44B fluorescence spectrophotometer [source]. The emission maxima was observed for the duplex at an excitation wavelength of 306 m$\mu$ and 524 m$\mu$. Furthermore, at 524 m$\mu$ there was essentially no excitation of EthBr. Accordingly, the 524 m$\mu$ wavelength is suitable for excitation of intercalated EthBr. A laser with filters passing only the 524 m$\mu$ wavelength can provide this source for a fluorescence spot assay in the same manner that the fluorescence spot assay was conducted using a U.V. transilluminator.

C. Synthesis of THC-1-0-Hemisuccinic Acid and coupling to $(dT)_{10}$-NH$_2$

In a reaction flask, 25 mg of sodium hydride was added to a solution of 170 mg THC in 5 ml dry tetrahydrofuran. The reaction mixture was refluxed for 2 h under nitrogen. Then, a solution of 53.3 mg succinic anhydride was dissolved in 1 ml of THF and added to the reaction mixture. The reaction proceeded for four hours at 60° C. The final reaction mixture was diluted with 20 ml ethyl acetate and washed with 15 ml 1N HCl. The organic phase was dried with anhydrous sodium sulfate and evaporated to dryness in a vacuum centrifuge.

For the coupling reaction, the solutions were kept at 4° C. Fifty $\mu$g $(dT)_{10}$-amine was added to 0.7 ml Dulbeco's PBS, pH 7.4. To that solution, 23 $\mu$g 1-(dimethylaminopropyl)-3-ethylcarbodiimide hydrochloride (EDCI) in 0.23 ml PBS and 25 $\mu$g of 9-tetrahydrocannabinol-1-0-hemisuccinic acid in 0.25 ml of 1:2 puridine: 1,4-dioxine, were added sequentially. The reaction mixture was incubated overnight at 4° C. and purified by HPLC as shown in FIG. 2. The analyte-oligonucleotide complex was isolated as a single sharp peak. Alternatively, any of the synthesized analyte-oligonucleotide complexes may be purified by affinity chromatography using a complementary oligonucleotide affinity adsorbent material.

Thus, while there have been described what are presently the preferred embodiments of the present invention, other and further changes and modifications could be made thereto without departing from: the scope of the invention, and it is intended by the inventor herein to claim all such changes and modifications.

I claim:

1. A kit for performing a competitive nucleic acid immunoassay for the detection of analytes, comprising in at least one container:
   (a) an analogue of an analyte-oligonucleotide complex;
   (b) a complementary oligonucleotide chain for conjugating with the analogue-oligonucleotide complex;
   (c) an antibody specific for the analogue, said analogue competes with said analyte for binding with said antibody, and said analogue-oligonucleotide complex competes with said analyte for binding to said antibody; and,
   (d) a labelling means having an affinity for a nucleic-acid duplex formed from said analogue-oligonucleotide complex and said complementary oligonucleotide chain,
   whereby the presence of said labelling means in said nucleic-acid duplex can be detected, and the detection of the labelling means indicates the presence of the analyte in a test sample.

2. The kit recited in claim 1, wherein said analogue includes said analyte.

3. The kit recited in claim 2, wherein said labelling means includes a fluorescent dye.

4. The kit recited in claim 3, wherein said fluorescent dye is selected from the group consisting of: DAPI, DIPI, H33258, acridine orange, acridine yellow, 288/45 and ethidium bromide.

5. The kit recited in claim 4, wherein said labelling means can be detected by a detection means is selected from the group consisting of: a shortwave U.V. transilluminator, a U.V. lightbox and fluorescence spectrophotometer, for detecting the color intensity and fluorescence of said dye.

6. The kit recited in claim 5, further comprising a solid phase for immobilizing a component of said kit and a developer fluid including the remaining components of said kit,
   whereby said solid phase may be contacted with said sample to be analyzed, and then contacted with the developer.

7. The kit recited in claim 6, wherein said solid phase include the components of said kit immobilized in a soluble retention means on said solid phase,
   whereby when said solid phase is contacted by a fluid sample to be analyzed, the sample or the carrier of such sample dissolving said retaining means and allows the components of said kit to be combined with said sample.

8. The kit recited in claim 1, wherein said labelling means is covalently bound to said analogue-oligonucleotide complex or to said complementary oligonucleotide chain.

9. A method for performing a competitive nucleic acid immunoassay for detection of analytes in a sample comprising the steps of:
   (a) obtaining a sample to be analyzed for the presence of an analyte;
   (b) combining an antibody specific for an analogue of said analyte with said sample, said analogue competes with said analyte for binding with said antibody;
   (c) combining an analogue of said analyte-oligonucleotide complex with said sample, said analogue-oligonucleotide complex competes with said analyte for binding to said antibody;
   (d) combining a complementary oligonucleotide chain to said analogue-oligonucleotide complex for conjugating with said sample;
   (e) combining a labelling means, having an affinity for a nucleic-acid duplex formed from said analogue-oligonucleotide complex and said complementary oligonucleotide chain, with said sample; and,
   (f) detecting the presence of the labelling means in said nucleic acid duplex,
   whereby the presence of the label in said nucleic acid duplex indicates the presence of the analyte in the sample.

10. The method recited in claim 9, wherein the said labelling means is covalently bound to said analogue-oligonucleotide complex or to said complementary oligonucleotide chain.

11. The method recited in claim 9, wherein the said analogue includes the analyte.

12. The method recited in claim 11, wherein said labelling means includes a fluorescent dye.

13. The method recited in claim 12, wherein said fluorescent dye is selected from the group comprising: DAPI, DIPI, H33258, acridine orange, acridine yellow, 288/45, 186/134, and ethidium bromide.

14. The method recited in claim 13, further comprising visual examination of said sample to detect color intensity and fluorescence of said dye utilizing a detection means selected from the group consisting of short-wave U.V. transilluminator, a U.V. lightbox and fluorescence spectrophotometer.

15. The method of claim 9, wherein,
   (i) steps a, b, and c are performed by contacting a solid phase with said sample, the solid phase containing said antibody specific for the analogue of said analyte, and said analogue-oligonucleotide complex immobilized on the solid phase, and,
   (ii) steps d and e are performed by then contacting said solid phase with a developing solution containing the complementary oligonucleotide complex to said analogue-oligonucleotide chain and said labelling means.

16. The method recited in claim 15, wherein said labelling means is covalently bound to said analogue-oligonucleotide complex or to said complementary-oligonucleotide chain.

17. The method recited in claim 16, wherein the said analogue includes the analyte.

18. The method recited in claim 17, wherein said labelling means includes a fluorescent dye.

19. The method recited in claim 18, wherein said fluorescent dye is selected from the group comprising: DAPI, DIPI, H33258, acridine orange, acridine yellow 288/45, 186/134, and ethidium bromide.

20. The method recited in claim 19, further comprising visual examination of said sample to detect color intensity and fluorescence of said dye utilizing a detection means selected from the group consisting of short-wave U.V. transilluminator, a U.V. lightbox and fluorescence spectrophotometer.

21. The method of claim 9, wherein,
   (i) steps a, b, c, d, and e are performed by contacting a solid phase with said sample, the solid phase containing said antibody specific for the analogue of said analyte, said analogue-oligonucleotide complex, said complementary oligonucleotide chain and said labelling means, immobilized by a soluble immobilizing means upon the solid phase, and preventing said components from interacting prior to said immobilizing means being solubilized,
   whereby contacting said solid phase with a fluid containing said sample dissolves said immobilizing means and allows said components to react with said sample.

22. The method recited in claim 21, whereby said labelling means is covalently bound to said analogue-oligonucleotide complex or to said complementary-oligonucleotide chain.

23. The method recited in claim 22, wherein said analogue includes the analyte.

24. The method recited in claim 23, wherein said labelling means includes a fluorescent dye.

25. The method recited in claim 24, wherein said fluorescent dye is selected from the group comprising: DAPI, DIPI, H33258, acridine orange, acridine yellow, 288/45, 186/134, and ethidium bromide.

26. The method recited in claim 25, further comprising visual examination of said sample to detect color intensity and fluorescence of said dye utilizing a detection means selected from the group consisting of short-wave U.V. transilluminator, a U.V. lightbox and fluorescence spectrophotometer.

* * * * *